(12) United States Patent
Stegehuis et al.

(10) Patent No.: US 10,709,395 B2
(45) Date of Patent: Jul. 14, 2020

(54) RADIATION SYSTEM

(71) Applicant: KONINKLIJKE PHILIPS N.V., Eindhoven (NL)

(72) Inventors: Herman Stegehuis, Best (NL); Heidrun Steinhauser, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/315,712

(22) PCT Filed: Jul. 5, 2017

(86) PCT No.: PCT/EP2017/066758
§ 371 (c)(1),
(2) Date: Jan. 7, 2019

(87) PCT Pub. No.: WO2018/007437
PCT Pub. Date: Jan. 11, 2018

(65) Prior Publication Data
US 2019/0142353 A1    May 16, 2019

(30) Foreign Application Priority Data

Jul. 6, 2016 (EP) ..................... 16178103

(51) Int. Cl.
*A61B 6/10* (2006.01)
*A61B 6/00* (2006.01)
*G21F 3/00* (2006.01)

(52) U.S. Cl.
CPC ............ *A61B 6/107* (2013.01); *A61B 6/4452* (2013.01); *G21F 3/00* (2013.01); *A61B 6/4423* (2013.01); *A61B 6/4464* (2013.01)

(58) Field of Classification Search
CPC ..... A61B 6/107; A61B 6/4452; A61B 6/4423; A61B 6/4464; G21F 3/00
(Continued)

(56) References Cited

U.S. PATENT DOCUMENTS 6,325,538 B1    12/2001  Heesch
7,441,955 B2    10/2008  Guyonnet
(Continued)

FOREIGN PATENT DOCUMENTS

DE    102006058234 A1    6/2008
DE    102012212104 A1    1/2014
(Continued)

OTHER PUBLICATIONS

Goulet, M. et al "High Resolution 2D Dose Measurement Device based on a few Long Scintillating Fibers and Tomographic Reconstruction", Medical Phys. vol. 39, No. 8, pp. 4840-4849, 2012.

*Primary Examiner* — Courtney D Thomas

(57) ABSTRACT

A radiation system (50), comprising a patient support platform (3). An X-ray radiation source (2a, 2b, 2c) is positioned beneath the patient support platform and enclosed by fixed radiation shielding. An X-ray radiation detector (22) is positioned above the patient support platform. A detector X-ray radiation shield (1, 11) comprising shield extension (7) is arranged on either side of the patient support platform, which extend from the X-ray radiation 5 detector to the fixed radiation shielding. The shield extensions are able to be moved relative to the source radiation shield to allow access to a patient on the support platform.

15 Claims, 6 Drawing Sheets

(58) Field of Classification Search
USPC .......................................................... 378/203
See application file for complete search history.

(56) References Cited

U.S. PATENT DOCUMENTS

| | | |
|---|---|---|
| 2005/0236588 A1 | 10/2005 | Ein-Gal |
| 2006/0182227 A1 | 8/2006 | Bernhardt |
| 2008/0031422 A1 | 2/2008 | Barkow |
| 2009/0110152 A1 | 4/2009 | Manzke |
| 2009/0232282 A1* | 9/2009 | Belson ............... A61B 6/107 378/203 |
| 2012/0241652 A1 | 9/2012 | Jeschke |
| 2014/0054474 A1 | 2/2014 | Rees |
| 2014/0055271 A1 | 2/2014 | Chowdhary |
| 2014/0153700 A1 | 6/2014 | Belson |
| 2016/0029980 A1 | 2/2016 | Osherov |

FOREIGN PATENT DOCUMENTS

| | | |
|---|---|---|
| DE | 102013214222 A1 | 1/2015 |
| JP | H0513407 U | 1/1993 |

\* cited by examiner

RADIATION SYSTEM

CROSS-REFERENCE TO PRIOR APPLICATIONS

This application is the U.S. National Phase application under 35 U.S.C. § 371 of International Application No. PCT/EP2017/066758, filed on Jul. 5, 2017, which claims the benefit of European Patent Application No. 16178103.4, filed on Jul. 6, 2016. These applications are hereby incorporated by reference herein.

FIELD OF THE INVENTION

The technical field relates generally to radiation shielding in X-ray radiation systems for medical purposes.

BACKGROUND OF THE INVENTION

Exposure to radiation such as X-rays can be harmful. Medical staff must be close to a patient during X-ray guided interventions using an X-ray system so can be exposed to harmful scatter radiation. To avoid harm by scatter radiation it is known to wear heavy and uncomfortable lead aprons. A fixed radiation shield is shown in U.S. Pat. No. 6,325,538. U.S. Pat. No. 6,325,538 discloses a shield apparatus that includes spaced apart tapered sections, each being constructed in the nature of a bellows, and a central, rectangular housing. The rectangular housing is fitted to a patient support table and provides openings that accommodate a patient's head, arms, and lower torso. This fixed radiation shield reduces the need for an operator to wear extensive lead aprons. Such a radiation shield is not, however, ideal as it substantially limits accessibility to a patient positioned within the shield. In particular, the rectangular housing fitted to the table makes it difficult to access a patient within the shield apparatus and makes it difficult for a patient to get on and off the patient support table.

SUMMARY OF THE INVENTION

Hence, there may be a need to provide an improved and facilitated way of shielding operatives of X-ray radiation systems from harmful radiation.

The object of the present invention is solved by the subject-matter of the independent claims; wherein further embodiments are incorporated in the dependent claims.

In one aspect, there is provided a radiation system, comprising: a patient support platform; at least one X-ray radiation source positioned beneath the patient support platform; an X-ray radiation detector positioned above the patient support platform; a fixed source X-ray radiation shield disposed about the X-ray radiation source; a detector X-ray radiation shield comprising at least one shield extension able to be arranged to extend from the X-ray radiation detector to the source radiation shield and able to be moved relative to the source radiation shield to allow access to a patient on the support platform.

The source X-ray radiation shield is fixed in that it is not intended to be moved (as compared to shielding disposed with respect to the source in a C-arm system). The source X-ray shield may be fixed relative to an imaging room within which it is disposed and/or fixed to a floor. The detector X-ray radiation shield and/or the radiation detector and/or the patient support platform may also be movable relative to the fixed source X-ray radiation shield.

The source radiation shield is able to shield an operator from X-ray radiation scattering outwards from beneath the patient support platform and on all sides. The detector shield is able to shield an operator from X ray radiation scattering outwards from between the detector and the source shield. The at least one shield extension is able to be moved relative to the source radiation shield to allow access to a patient on the table and also to allow a patient to get on and off the patient support platform. Such independent movability of the at least one shield extension and the source shield provides ease of access to the patient support platform. Such movement is possible in a number of ways as described below.

The source shield may extend to the patient support platform so that, if the detector shield is moved, scatter radiation is shielded from emanating from between the patient support platform and the radiation source.

The detector shield extension may comprise a shield carrier and the at least one shield extension extending therefrom. The shield carrier may be part of the detector or a separate component mountable to the detector.

The radiation shield may be movable in the direction of the platform relative to the radiation detector or the detector and the radiation shield may move in conjunction. The radiation detector may be movable between a spaced position relative to the platform and an approximated position relative to the platform defining a detector gap. The shield extension is able to be arranged to bridge the detector gap. The shield extension is able to be retracted to a stowed configuration relative to the shield carrier to open the gap even when the radiation detector is in the approximated position. At least one displacement mechanism may be included in the system for moving the shield carrier between the first and second positions and/or moving the detector between the spaced and approximated positions.

The radiation system may comprise at least one displacement mechanism for moving the shield carrier toward and away from the patient support table. In this way, the shield extension may be moved relative to the patient support table. The displacement mechanism may be motorized and/or electrically powered.

The shield carrier may be part of the radiation detector so that the at least one displacement mechanism moves the radiation detector toward and away from the patient support table. Alternatively, the shield carrier may be a separate component from the radiation detector. The at least one displacement mechanism may be configured to move the detector toward and away from the patient support table.

The at least one displacement mechanism may be configured for moving the shield carrier relative to the radiation detector. Further, the at least one displacement mechanism is configured to move the radiation detector relative to the patient support table. In this way, the detector can be moved into place relative to the patient with view unobstructed by the shield and thereafter the shield can be moved into place for operator safety.

The radiation system may include a controller and a sensor. The sensor is for sensing positional information of a patient on the support platform. The controller is responsive to the sensed positional information to control an electronic mechanism, such as the above described at least one displacement mechanism, for positioning at least one of the detector, the shield and the at least one shield extension relative to the platform. In this way, optimal shielding and radiation detection, that is responsive to patient size and position, can be achieved in an automated way.

The at least one shield extension is able to be retracted relative to the shield carrier to a stowed configuration and extended relative to the shield carrier in an extended configuration or the at least one shield extension is removable from the shield carrier. Such retractability or removability allows the shield extension to be moved relative to the source shield for access to the patient support platform. Further, removability can assist in sterilization. Again, the shield carrier may be part of the radiation detector.

The radiation shield may include the form of a radiation shielding enclosure hood extending around the radiation detector. The hood extends around the detector to shield X-ray radiation on all sides. The at least one shield extension is included in the radiation shielding enclosure hood.

The radiation shield may comprise long sides on opposed sides of the patient support table and short sides extending between the long sides at each end, where short and long here is to be understood in the direction from the radiation detector to the patient support platform. The long and short sides together form the enclosure hood. The long sides are usually formed by the at least one shield extension. The long sides ensure sufficient operator protection whilst the short sides serve to meet the contours of the table or the patient on the table. The radiation shielding enclosure hood shields scatter radiation on all sides of the detector. The long sides forming the at least one shield extension are movable relative to the source radiation.

The enclosure hood may extend from a first end of the shield carrier/detector and be open at an opposite end to the first end. The enclosure hood may be attached to the shield carrier/detector at the first end and the opposite end may hang freely.

The enclosure hood may drape or hang from the shield carrier/detector.

The radiation shield may include a flexible shielding material, such as a textile. The material of the radiation shield may include flexible shielding material to allow conformance with the contours of the patient and the patient support platform.

The at least one shield extension may include indicator elements to provide an indication of incident radiation. The indicator elements may be radiation sensitive fibers and/or electronic devices associated with the at least one shield extension. Such indicator elements may provide an early indication of where shield reinforcement is required and/or where operators should not stand.

The at least one shield extension may detachable from the shield carrier/detector such as by way of a removable attachment. The removable attachment may be Velcro, magnetic, claps, buttons, etc.

The at least one shield extension may be attached to the shield carrier/detector at one end and hang freely at an opposite end.

The at least one shield extension may be formed from a plurality of shield extension elements. The at least one shield extension may hang or drape from the shield carrier or detector and be formed from a plurality of adjacent shield extension elements such as strips that are each attached at one end and free at the opposite end. Such a configuration improves flexibility and movability for access. For example, the extension elements may be able to be moved apart and thus moved relative to the source shield. The plurality of shield extension elements may be arranged in any convenient manner such as side-by-side and/or arranged in layers one upon the other. The plurality of shield extension elements may provide a continuous radiation attenuation barrier.

The source shield may comprise a platform flap or skirt extending from the patient support table that engages with the at least one shield extension. A flap or skirt may extend from each of opposed edges of the support platform. In such embodiments, the shield extension may extend beyond the platform.

The radiation source may comprise a plurality of radiation sources providing radiation at different angles with respect to one another or a radiation source that is movable to provide radiation at different angles. The radiation sources or the movable radiation source may be disposed within a shielded enclosure formed by the source shield. The radiation sources may be adapted to act collectively and/or individually. In such embodiments direct radiation beams may be produced from each radiation source. These direct radiation beams may be incident upon the patient and table whereby different scatter radiation patterns are created by the patient and table.

The plurality of radiation sources may comprise at least one movable radiation source and/or at least one stationary radiation source. The at least one movable radiation source may comprise plural radiation sources that are movable in conjunction or individually. The radiation sources may comprise groups of separately movable sources or all radiation sources may be movable. The plurality of radiation source may all be movable, all be stationary or include a mixture of movable and stationary radiation sources.

The source shield may be a fixed shield relative to the patient support platform and may be provided in the form of a shield enclosure such as a box.

The fixed shield may shield underneath the at least one radiation source and to the sides of the radiation source and allow radiation beams to be directed to the patient in an upward direction toward the patient support platform.

The at least one shield extension may comprise first and second shield extensions on opposed sides of the patient support platform that each extend to the source shield. Thus, the shield extensions may extend at least to a level of the source shield to avoid any gaps allowing scatter radiation to seep out. The opposed shield extensions may be located on respective sides of the platform that are able to be arranged to extend at least to the platform.

The shield extension may be able to be formed into a roll of radiation inhibiting material. This allows the at least one shield extension to move relative to the patient support platform and to provide access thereto.

The shield carrier/detector may be moveable between a first position and a second position such as by way of a displacement mechanism as described above. The platform and the shield carrier/detector may be spaced by a gap in the second position less than a corresponding gap in the first position. The shield extension extends at least across the gap when the shield carrier is in the second position. The shield extension may not extend across the gap or only partly across the gap when the shield carrier/detector is in the first position. The shield extension may be able to be arranged in a stowed configuration relative to the shield carrier/detector so that access to the platform is provided even when the shield carrier is in the second position by way of a gap between the shield carrier and the platform and wherein the shield extension is able to be deployed from the stowed configuration to bridge the gap. The shield extension may be retracted to the stowed configuration by rolling and securing to the extension carrier, e.g. by way of clips, or the shield extension may be retracted by way of a refraction mechanism.

The platform may be a table for a patient.

The radiation source may be provided in a shielded enclosure, such as a box, which forms at least part of the source shield. Such a shielded enclosure or box may only allow direct radiation towards the platform.

In the embodiments described herein, at least the extension shield may be wrapped or disposed within removable sterile covering material such as plastic. This feature can add in sterile processing after a procedure on a patient.

DESCRIPTION OF THE DRAWINGS

The exemplary embodiments will hereinafter be described in conjunction with the following drawing figures, wherein like numerals denote like elements, and wherein.

DETAILED DESCRIPTION OF THE EMBODIMENTS

Figure 1:
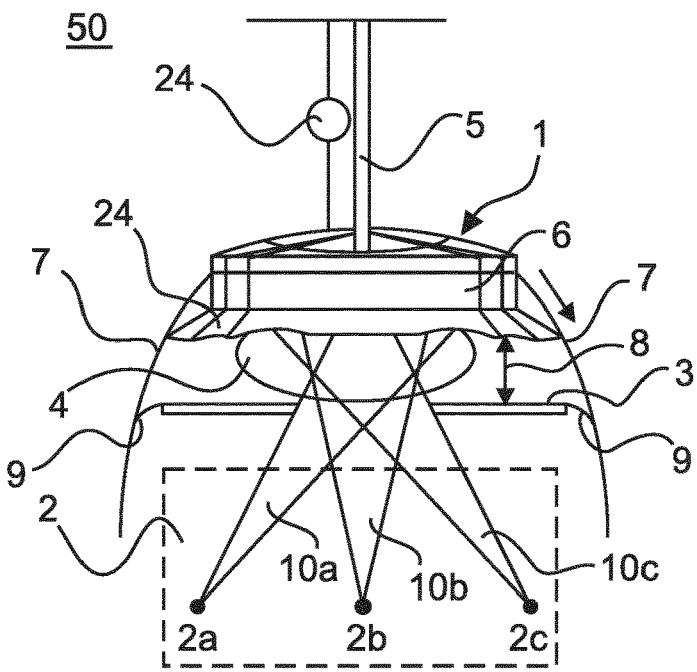
FIG. 1 is a schematic illustration of a radiation system with shield extensions in a deployed configuration engaging a platform flap or skirt.

The following detailed description is merely exemplary in nature and is not intended to limit the application and uses. Furthermore, there is no intention to be bound by any expressed or implied theory presented in the preceding technical field, background, brief summary or the following detailed description.

Operators of radiation systems emitting scatter X-ray radiation can be subject to exposure to potentially harmful levels of scattered radiation if they are not suitably shielded from the radiation. X-ray guided interventions by medical staff mean such staff must be close to a platform or table upon which their patient is located. Lead aprons for operators are known. Lead aprons are heavy and uncomfortable, so even simply reducing the level of scatter radiation may allow lighter more comfortable aprons to be used.

By exemplary aspects, a radiation shield of a radiation system provides radiation scatter attenuation from a patient subject to direct radiation. One or more X-ray radiation sources may be provided in a shielded enclosure or box with an X-ray transparent side or aperture so that direct radiation is incident upon a subject. The radiation source or sources are below the patient. The patient is supported on a platform such as a table. The radiation in such circumstances projects upwards towards the patient, through the platform and the patient, and beyond to an X-ray radiation detector of the radiation system. The box for the radiation source has fixed radiation shields to prevent escape of radiation directly towards an operator, particularly beneath and on all sides of the radiation source or sources. An upward incident angle for direct radiation beams towards the patient from the radiation source or sources mean that an operator close by, but to the side of the platform, is not in direct line with such direct radiation. Scattered radiation, from the patient and other elements such as the platform itself, positional supports for the patient etc., are the main concern. Generally, upward and downward scattered radiation will not be incident upon an operator. It is a lateral band of scattered radiation which is problematic.

Above the patient in the radiation system is the radiation detector. The detector is moveable in a vertical or height direction to facilitate location and positioning relative to a patient upon a platform. Once the patient is in position on the platform, then the radiation detector is moved near the patient for a desired field of view and the patient subjected to direct radiation.

In exemplary embodiments, movement of the detector is by a displacement mechanism. In some embodiments, the radiation shield is movable relative to the detector by the same displacement mechanism or another displacement mechanism. In other embodiments, the radiation shield is mounted to, or part of, the detector and thus moves in conjunction therewith. In embodiments, a shield carrier of the radiation shield is positioned near a patient with the radiation detector in position for detection. There is a gap between the carrier/detector and the platform through which scattered radiation may be incident upon an operator to the side of the platform, if not for further shielding as described below. The shield carrier may be attached to, or part of, the detector so that they can move in conjunction.

In some embodiments, the radiation source is located in a shielded box, which is stationary when radiation imaging is performed. Some other radiation systems have a so-called C-arm in which the source and the detector are co-rotated. Use of a stationary shielded enclosure is facilitated by the use of at least one movable X-ray source or an array of stationary X-ray sources or a combination of movable and stationary X-ray source in the shielded radiation source box or enclosure. The at least one source or the array of sources are able to aim radiation at different angles which can be picked up by the radiation detector for imaging purposes. The images provided can be used for live guidance of a surgical device within a patient such as location of orthopedic pins in or about bones, catheters or other medical devices. However, either with an array of radiation sources or co-rotation of a radiation source(s) on a C arm or a robotic arm, operators, such as medical staff, are then exposed to scattered radiation which may be more difficult to predict due to the differing direct radiation beams from the radiation sources.

In some exemplary embodiments, the shield carrier need not have any or too great a radiation attenuation effect. If the incident scattered radiation upon the shield carrier has a sufficiently inclined angle, then it is not incident upon an operator. Further, the detector generally comprises its own shield plate to substantially attenuate radiation passing in an upward direction. Scatter radiation can pass through a gap between the detector and the platform. Associated with the shield carrier is a shield extension.

In some embodiments, the shield extension is retractable so that the shield extension is normally stowed as the shield carrier/detector is displaced from a first position to a second position. In other embodiments, the shield extension does not have a stowed configuration and may be permanently down or removable. In a stowed configuration, the shield extension that would bridge the gap when the shield carrier/detector is in the second position are stowed relative to the shield carrier by rolling, retraction, etc. thereof. In the first position of the shield carrier/detector, the radiation shield, particularly if the shield extension is in a stowed configuration, is sufficiently spaced with a gap from the platform to allow a patient to be located on the platform. The shield extension may be otherwise moved to allow the patient to be located on the table such as by parting strips thereof or by removal of the shield extension.

In the second position, the shield carrier/detector is nearer the platform with the gap reduced. In various embodiments, once the shield carrier is in position adjacent the patient, then the shield extension is deployed to extend at least to the platform across the reduced gap and to extend to the shielding of the source shield (which may include the shielded enclosure and the table flaps or skirt). In other embodiments, the shield extension is attached to the shield carrier/detector. In yet other embodiments, the shield extension is moved with the shield carrier/detector to bridge the gap.

The radiation shield creates a shielded enclosure hood, which is open at a free end hanging from the shield carrier/detector. The shielded enclosure hood is closed by the platform and the patient to create a shielded enclosure when the shield extension extends across the gap to the platform. The combination of shielding of the detector, shielding of the source and the shielding of the enclosure hood shield X-ray radiation in all direction (up, down and all sides). The shield extension stops or attenuates to a manageable extent scattered radiation exiting the patient towards an operator. In embodiments, first and second shield extensions are provided that respectively extend from the detector at least to the platform, on each lateral side of the platform. The stopping or attenuation of scattered radiation by the shield extensions is in a band of incident angles potentially through the gap. Blocking or attenuation reduces incidence of scatter radiation upon an operator beside the radiation system.

In various embodiments, the shield will include radiation shielding material completely surrounding the part of the patient or patient subject to direct radiation by forming a radiation shielding enclosure hood. However, provided an operator is aware of 'no-go' sectors then partial surround of the patient by the radiation shield forming a hood may be acceptable. The shield extension provides scatter radiation attenuation in those portions or sectors of the periphery of the platform or table enclosed, whilst those sector or portions not engaged or enclosed will be 'open' to scatter radiation. The open areas to scatter radiation will be known to the operator as 'no go' sectors about the patient or areas where higher levels of protection with heavier uncomfortable lead aprons will be needed. In one exemplary embodiment, the shield includes at least one shorter fringe shield made of radiation blocking material extending around one or more parts thereof for contact with the patient and the shield extension that extends beyond the fringe shield to the platform. The fringe shields may thus attenuate radiation at, for example, feet and head ends of the patient by contact therewith and shield extensions may be located adjacent arms or sides of the patient. The shield fringes and the shield extensions may together substantially completely surround the patient to form the radiation shielding enclosure hood.

In various embodiments, the shield carrier may provide limited if any scattered radiation attenuation when it is a separate component from the detector. Radiation attenuation by the carrier itself may not be essential.

In embodiments, the shield carrier will be part of, or mounted to (possibly movably mounted to), the detector and thus above the patient or at least level with an upper part of that patient. A gap between that carrier and the platform upon which the patient is positioned. This gap is closed to enclose the primary radiation beam by the shield extension. Scattered radiation passing the gap towards an operator such as medical staff is at least subject to acceptable attenuation by the shield extension.

In some embodiments, the shield extension is generally flexible and may be detachable from the shield carrier for cleaning and sterilization. It will be understood that the shield carrier may be part of the radiation detector housing or a separate component. When a separate component, the shield carrier may include an opening for receiving a part of the radiation detector. The shield carrier may be detachable from the radiation detector, in addition to or alternatively to, the shield extension being detachable. Having the shield extension detachable from the carrier/detector (and/or the shield carrier detachable from the radiation detector) allows, in addition to cleaning and sterilization, the choice of different shield extensions for different circumstances. Respective shield extensions can provide different levels of scatter radiation attenuation for different radiation beam intensities and/or types. Readily inter-changeable shield extensions may also allow more efficient operation. If there is a possibility of cross-infection or contamination between patients or patients, then shield extensions can be quickly changed. Regular calibration of the effectiveness of the shield extension for scatter radiation attenuation can be performed if needed by detaching the shield extension.

The radiation shield through the shield extension produces a band or partial band of radiation attenuation for scattered radiation rather than an essential need for the whole radiation shield to be uniformly effective in terms of scatter radiation attenuation. This may make radiation shield construction less complex. Conflicts with the radiation detector providing a true response due to radiation absorption and/or attenuation materials distortion issues nearby can also avoided.

The shield extension may be formed of a fabric or be covered on the outside with a smart fabric which includes indicators such as radiation detection fibers and/or electronics. In such circumstances, operators can be warned of a lack of sufficient scattered radiation attenuation by changes to the detection fibers and/or electronic radiation sensor reports either contemporaneously and/or by post operation review. These radiation reviews and summaries may also be used for monitoring operator radiation dosages. The nature of radiation scatter about a patient is not uniform or sometimes even stable so 'tell-tale' indicator radiation detection fibers and/or electronics may be of assistance with regard to informing an operator as to zones or sectors with high levels of scatter radiation.

In various exemplary embodiments, the shield extension, and other shielding part of the radiation shield, will be flexible in terms of the material, such as textiles, from which it is formed. Flexibility may be achieved from the nature of the material from which the shield extension is made. Alternatively, or additionally, flexibility may be achieved by presenting a number adjacent flaps or strips to provide some articulation between the flaps or strips. The flaps may be free to move relative to each other subject to providing a continuous radiation attenuation barrier in the attenuation band across the gap between the carrier and the platform. The flaps may partly overlap with respect to adjacent flaps. The flaps may be pinned with over-lapping edges together or otherwise located in the shield extension.

A convenient way of stowage of the shield extension is by rolling it either as a whole or as individual flaps about the side or edge of the shield carrier. Alternatively, the shield extension could be folded or comprise panels designed to slide past each other as the shield extension drops or is lowered down towards the patient/platform to complete enclosure of the direct radiation beam. The shield extension may stretch or telescope or unfold as it is lowered towards the platform of a radiation system.

In some embodiments, the shield extension may be lowered to at least a level of the platform table. To ensure a good enclosure and attenuation of scatter radiation, the shield extension will in other embodiments extend well beyond the platform peripheral edge to ensure complete enclosure and so scatter radiation attenuation. In particular, the shield extension should extend to at least a level of shield of the source, which includes at least the flap or skirt attached to the table and the source box.

A platform skirt or flap can be secured to the platform table peripheral edge to overlap with the shield extension in use. The platform flap may have an outward arch configuration. An overlapping shield extension abuts the platform flap or skirt, possibly under gravity, so ensuring a pressing face to face overlap engagement with less possibility of gaps between them through which scatter radiation may escape to be incident upon an operator. The platform skirt or flap provides a radiation shielding function.

FIGS. 1 to 3 and 5 provide schematic illustrations of one embodiment of a radiation system 50 including a radiation shield 1. The radiation system 50 has a radiation source 2, a platform 3 for a patient 4, a radiation detector 22 and at least one displacement mechanism 5, 24. The shield 1 generally includes shielding material 7, 24 in a hood or hat like configuration. The shield 1 has a shield carrier 6 suspended upon the shield displacement mechanism 24 for raising and lowering the shield 1 relative to the patient support platform 3. The detector 22 is suspended from the detector displacement mechanism 5 for raising and lowering the detector 22. The detector displacement mechanism 5 and the shield displacement mechanism 24 may be the same displacement mechanism or separate displacement mechanisms. The detector 22 and the shield 1 may be movable relative to one another or move in conjunction. The patient 4 is presented upon the platform 3.

At least one shield extension 7 is associated normally about a periphery of the shield carrier 6. In the shown embodiment, first and second shield extensions 7 are included in the shield 1. Further, the shield 1 includes fringe shielding 24 arranged for contacting the patient on the platform 3 at head and leg ends and which extend around the detector 22/the carrier 6 between the first and second shield extensions 7. The fringe shielding 24 may extend all the way around the detector 22 or be positioned only at opposed ends. The shield extensions 7 and the fringe shielding together form a radiation shielding enclosure hood. The shield extensions 7 extend further in the direction from the detector 22 to the platform 3 (when deployed, if deployable) than the shorter fringe shielding.

The radiation system 50 further comprises at least one radiation source 2a, 2b, 2c disposed within a fixed shielded radiation enclosure or box 100. The platform 3, in this embodiment, has flaps or skirts 9 providing further shielding of radiation in cases where the radiation could scatter from the between the shielded box 100 and the platform 3. Thus, source shielding is provided by the skirt 9 and the box 100.

In the illustrated embodiments of FIGS. 1 to 5, a plurality of radiation sources 2a, 2b, 2c are included. One, some or all of the radiation sources 2a, 2b, 2c may be movable or one, some or all of the radiation sources 2a, 2b, 2c may be stationary or some combination of movable and stationary radiations sources 2a, 2b, 2c may be provided. When stationary, plural radiation sources 2a, 2b, 2c are directed at different angles. When movable, the radiation source or sources may be movable to different angles. The at least one radiation source 2a, 2b, 2c direct radiation beams 10a, 10b, 10c from each respective source 2a, 2b, 2c and are shown incident upon the patient 4. These beams 10a, 10b, 10c can be operated collectively and/or individually as part of an interventional radiation operation by an operator. Each beam 10a, 10b, 10c alone or in combination will create different scatter radiation from the patient 4. The radiation shield 1, and particularly the shield extension 7, can block these different and varying scatter radiation results.

The at least one radiation source 2 is at least one X-ray source. The X-rays produced by the at least one X-rays source will be scattered by incidence upon the patient 4. The radiation shield 1 is deployed in order to prevent such scattered X-rays becoming incident upon an operator such as a medical worker adjacent the radiation system 50. In particular, the at least on radiation source 2a, 2b, 2c is operatively associated with the detector 22, e.g. by at least one image processing unit, for producing electronic X ray imaging data, particularly tomographic imaging data.

The system 50 shown as exemplary embodiments in FIGS. 1 to 5 includes the at least one displacement mechanism 24, an electronic controller 52 and at least one position sensor 24. The position sensor 24 is configured to output sensed information indicative of a height above the platform 3 of the patient 4. The position sensor 24 may be at least one camera or plural cameras. The controller 52 is responsive to the sensed information to control the at least one displacement mechanism 5, 24 to automatically position the detector 24 and/or the radiation shield 1. The controller 52 may also be able to control an actuator (not shown) to automatically lower the shield extensions 7 (in embodiments where a stowed configuration is provided) to ensure overlap with source shielding 9, 100 in response to the sensed information. The controller 52 may determine the position of the detector 24 and/or the shield 1 and/or the at least one shield extension 7 with respect to the patient 4 on the basis of optimizing detection results and/or optimizing scatter attenuation.

The radiation shield 1 could be part of the original equipment as supplied with the radiation system 50 or a retro-fit shield 1 to an existing radiation system 50 utilizing an existing displacement mechanism 5 for a radiation detector 22 could be used.

Figure 3:
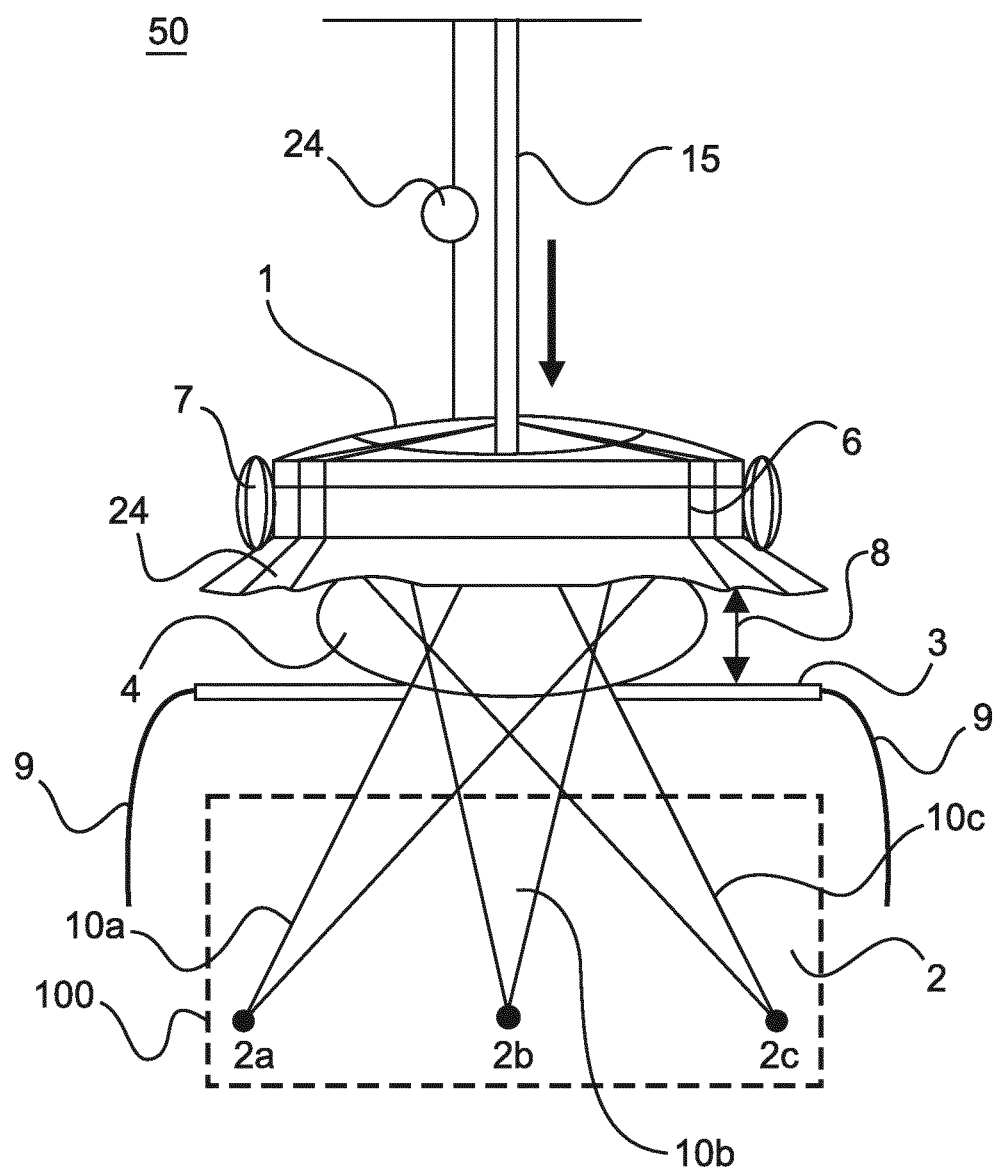
FIG. 3 is a schematic illustration of the radiation system depicted in FIG. 1 and FIG. 2 with the shield carrier in a second position; and, FIG. 4 is a schematic illustration of a radiation system similar to that depicted in FIGS. 1 to 3, but with no platform flap or skirt.
Figure 4:
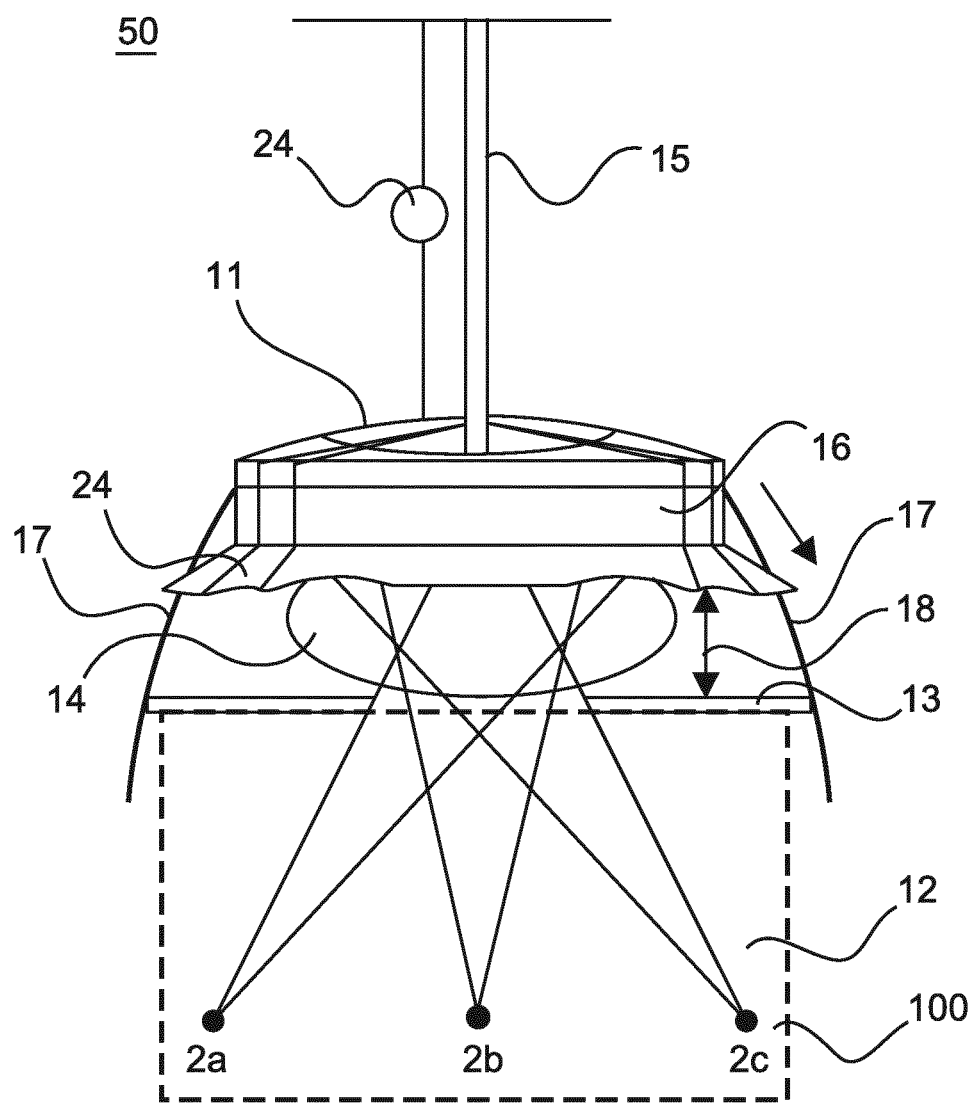
Figure 5:
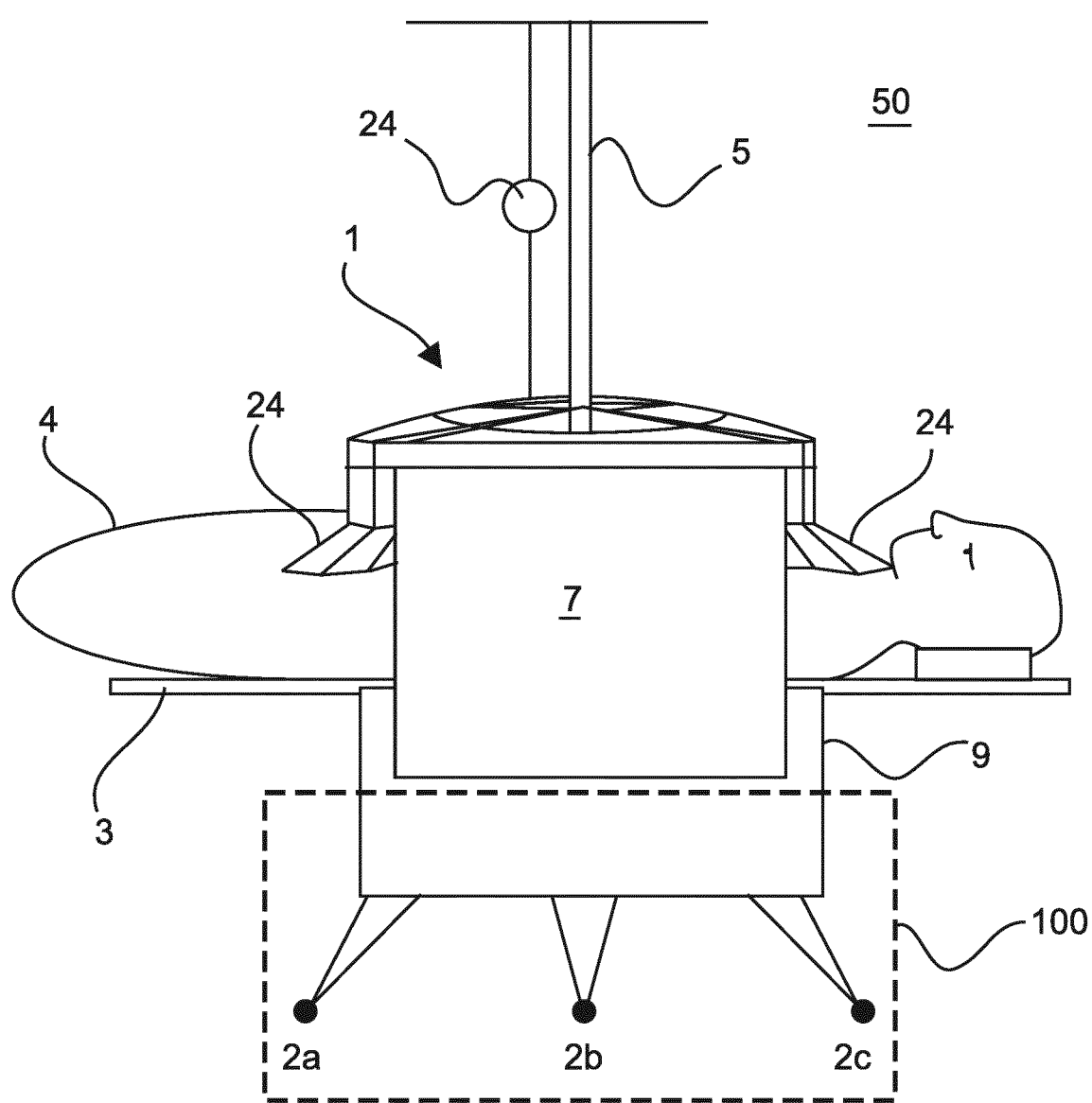
FIG. 5 is a schematic illustration of a radiation system according to that depicted in FIGS. 1 to 3 from a side view.

In the embodiments of FIGS. 1 to 5, the at least one shield extension is deployable from a stowed configuration. Other embodiments are described below with reference to FIGS. 6 and 7 in which the shield extension is not deployable in the same way. When deployed as depicted in FIGS. 1 and 5, the shield extension 7 is lowered and generally hangs down to extend beyond and below the carrier 6/the detector 22. In this deployed configuration, as depicted in FIGS. 1 and 5, the shield extension 7 extends across a gap 8 between the carrier 6 and the platform 3 to provide an enclosure about the patient 4 with a fringe shield (not shown).

Figure 2:
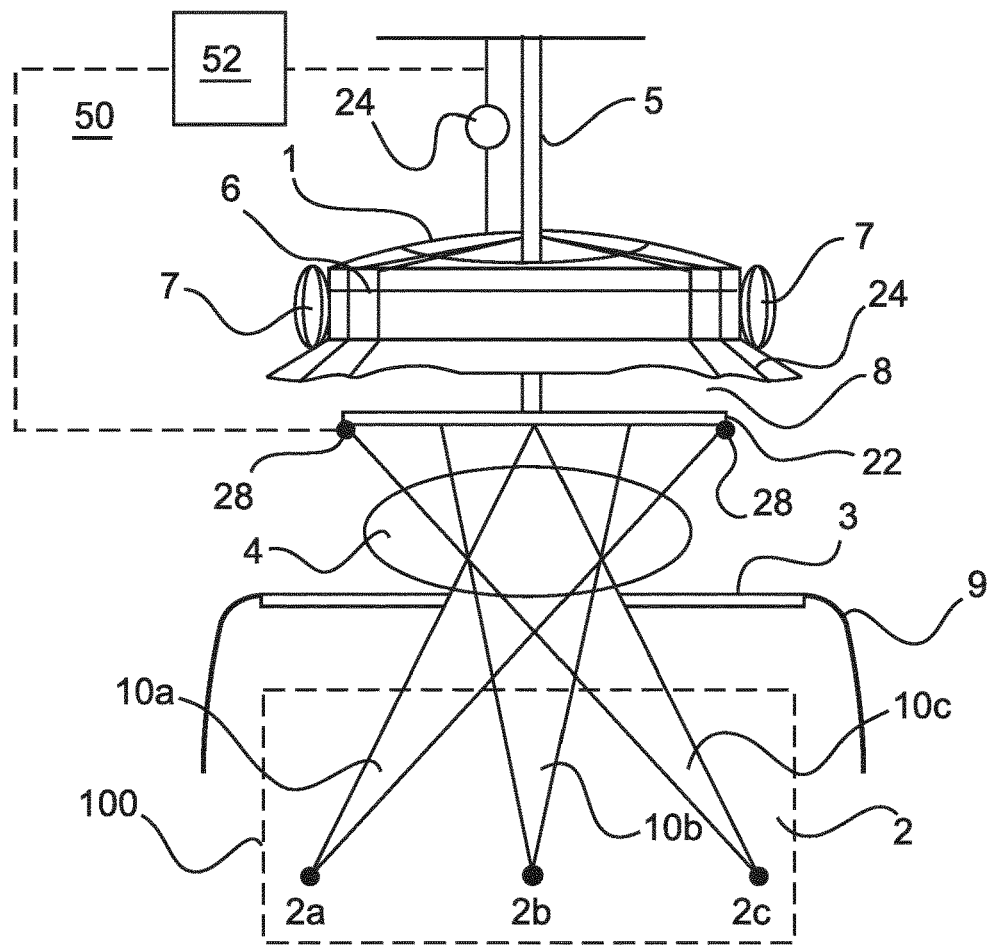
FIG. 2 is a schematic illustration of the radiation system depicted in FIG. 1 associated with a shield carrier in a first position.

As illustrated in FIGS. 1 and 5, the flap 9 engages the shield extension 7 in an overlapping side-by-side engagement to avoid open gaps through which radiation scatter may leak. Thus, the shield extension 7 may contact the source shielding provided by the flaps 9 in a gapless manner, i.e. no gap exists in the shielding through which scatter radiation could emanate. Further, the radiation shield 1 is able to be moved relative to the source shield by any one of a number of means such as moving the shield extension to a stowed configuration as shown in FIGS. 2 and 3, moving the shield carrier 6 or the detector 22 to a position further spaced from the platform 3 or moving slats of the shield extension apart, thereby allowing access to the patient 4 and the support platform 3. Exemplary alternative possibilities for relatively moving the shield extension and the platform 3/the fixed shielded enclosure 100 are described below with respect to FIGS. 6 and 7.

FIGS. 2 and 3 respectively, and schematically, illustrate the radiation shield 1 in positions during initial stages of deployment prior to the deployed configuration of the shield at least one shield extension 7 as illustrated in FIGS. 1 and 5. In a first position or configuration as depicted in FIG. 2, the radiation shield 1 and the detector 22 are raised above the platform 3 so that a patient 4 can be located upon the platform 3. The radiation source 2 will not be operative so the at least one radiation source 2a, 2b, 2c will not present active radiation beams to the patient 4 during initial stages of deployment when the patient is being located on the platform 3 as the radiation shield 1 and other parts of the radiation system 50 will not provide radiation protection.

FIG. 3 provides a schematic illustration of the radiation shield 1 in a second position at an intermediate stage of deployment. Thus, the shield carrier 6 is displaced with the shield extension 7 stowed. In the specific embodiment depicted in FIGS. 1 to 3, the shield extension 7 is rolled up for storage or stowage. Thus, with the carrier 6 in the first position as depicted in FIG. 2, and the radiation detector at an upper or initial position, the shield extension 7 does not present an obstruction to access by the patient 4. The stowed shield extension 7 is positioned out of the way to enable the patient 4 to be located on the platform 3.

The carrier 6 is movable downwardly and is lowered towards the patient 4 and platform 3. The carrier 6 can be lowered with the radiation detector 22 to a position close to the patient 4 for a good field of operation for the radiation detector 22. The shield carrier 6 is lowered to a desired spaced position relative to the platform 3, which is generally consistent with the patient 4 surface. The shield fringing may form part of an enclosure about the patient 4 or part of the patient inside the enclosure such as a patient torso.

However, even in this close position, the gap 8 to the sides of the patient 4 remains, although reduced from that in the first position and through which scattered radiation may emanate towards an operator such as medical staff. To prevent or at least attenuate that scatter radiation, the stowed shield extension 7 is deployed. The extension 7 is extended from the shield carrier 6 in the second position depicted in FIG. 3 to the deployed configuration relative to the shield carrier 6 depicted in FIG. 1. Respective shield extensions 7 may be extended from the shield carrier 6 on opposed sides of the platform 3 to close the gap on each of the sides of the patient. In the extended configuration, the at least one shield extension 7 should extend to source shielding, which includes the skirt 9 and the box 11 in this embodiment, preferably extending so far as to overlap the source shielding, thereby eliminating any gaps between the shields, as shown in FIG. 1. Thus, in the extended configuration, maximum scatter radiation attenuation can be achieved, while still allowing access to the patient 4 and the platform 3 in particular in the stored configuration.

The at least one shield extension 7 provides a band or partial band of radiation stopping or attenuation material. The at least one shield extension 7 may each comprise a sheet or a number of partially overlapping strips of radiation absorption and/or attenuating material. The extension 7 has sufficient width and/or depth of radiation absorption material such that at least incident scatter radiation angles from the patient 4 towards operators are blocked or attenuated. The extension 7 could be a single thickness of material or formed of a laminate of different layers of radiation attenuating material to stop or at least attenuate the level of scatter radiation incident upon an operator.

In the shown embodiments, first and second extension shield 7 are provided on opposed sides of the platform 3. It will be understood that several or a plurality of separate extension shields 7 could be associated with the carrier 6 or the detector 22 so that these extension shields 7 extend from suspended association with the carrier 6. The plurality of extension shields could lie over each other. A plurality of shield extensions allows variations in the attenuation effects of the deployed shield extension as a combination of over-laid separate shield extensions 7. Such variations in the extension shield 7 may accommodate differences in radiation sources, positions and orientation as well as any differences in scatter radiation patterns.

The shield extension 7 may incorporate smart materials such as textiles or fibers along with electronics to identify level and extent of scatter radiation incident upon the shield extension 7. Such smart materials and/or electronics may provide a read-out as to incident radiation scatter at different parts of the shield and/or provide an indicator or tell-tale color change for a more visible indication to an operator as to sections, sectors or zones of the radiation shield with higher and/or lower scatter radiation intensities. Electronic monitoring with sensors in the radiation shield 1 (possibly both the shield carrier 6 and/or the shield extension 7) allows the level of scattered radiation in different parts of the shield over time to be recorded for later analysis. Such analysis may enable the radiation shield 1 to be adjusted in terms of its radiation attenuation response by adding more layers of radiation absorption/attenuation material locally as required or an alternative shield extension 7 used.

In embodiments, the shield extension 7 is detachable from the carrier 6/the detector 22. The whole carrier 6 with extension 7 could be removed from the radiation system 50 but this may be less convenient, particularly if the carrier forms part of other components of a radiation system 50 such as the detector 22. This will allow cleaning and/or sterilization of the shield extension 7. Rendering the shield extension 7 easily detachable will also allow provision of a range of different shield extensions of different capabilities to be use. For example, different lengths of extension 7 may be available so that a range of depths of the gap 8 can be spanned by the appropriate choice of the extension 7. Such range of different lengths will ensure an adequate overlap with the edge of the platform 3 for closure of the enclosure about the table/platform 3 and the shielding of the radiation source 2, or more effectively engage with the skirt or flap 9 when used, without compromise with a one size fits all shield extension dimensions, which will be too big/long for some situations. The shield extension 7 could also be associated with a mechanism to allow selective extension only to a desired extent from a roll or other means of stowage of the extension 7 upon the carrier 6/detector 22. Thus, excessive lengths of the extension 7 may not dangle below the platform and become a nuisance.

The radiation shield 1 relates to scatter radiation from an interventional X-ray system having a radiation source box 100. The box 100 generally limits direct radiation exposure other than towards the patient 4. The radiation shield 1, through at least the shield extension 7, provides an enclosure which creates a 'barrier' by which outward scatter radiation towards an operator at the side is at least attenuated from the patient 4 such as a patient or any apparatus to mount or support the patient 4 or just any articles such as surgical equipment in the enclosure of shield 1 and the platform 3.

The radiation shield 1 itself provides a hood or hat like shape comprising fringe shielding 24 and the at least one shield extension 7, which act as an enclosure hood of shielding material open at one end until closed by engaging the platform 3 and patient 4 as the enclosure about the patient 4.

The shield 1 could include radiation shielding material that is short at head and foot ends provided mostly by fringe shielding 24 and long at lateral sides provided by the shield extensions 7 to close the gap 8 where an operator would stand. The shield 1 is of sufficient size so as to at least cover the torso of an adult human if that is the patient. The carrier 6 is located with respect to the detector so the detector 22 shields upwards radiation and the shield 1 also acts in the gap between the detector 22 and the platform 3. Further, the source shielding of the skirt 9 and the box 100 shields from radiation leakage from the platform 3 down. Accordingly, a highly effective and adaptable shielding arrangement is provided.

As indicated above, generally the radiation shield 1 will be provided around the edges of the radiation detector 22. In such circumstances, the shield carrier 6 can be part of the detector housing or a separate element, but either way the radiation shield 1 is preferably mounted so that the shield extension 7 can be lowered, either in a controlled manner or just fall (i.e. drape), to be at least level with the platform 3 to engage it. In the lowered state, the radiation shield 1, through the at least one extended shield extension 7, encloses completely the primary radiation beam such as an X-ray beam and stops or at least attenuates over its width/depth to an acceptable/desired level scatter radiation originating within the enclosure, particularly from the patient 4. Attenuation at least means lighter more comfortable lead aprons can be used by operators. The shield extension 7 could extend in a fixed way (i.e. be non-retractable), with a portion of the extension 7 below the carrier as a curtain which extends from the carrier 6, as will be described further with respect to FIG. 7 below.

A platform flap or skirt 9, which is also a radiation shield, as depicted in FIGS. 1 to and 5, is optional. A skirt or flap 9 may provide benefits in terms of providing a better enclosure, particularly if the flap or skirt 9 has some flexible resilience to drape out in an arch as shown. With such resilience, the shield extension 7 will be lowered as it is extended such that it lies over the skirt 9. The weight of the at least one extension 7 under gravity may act upon the skirt 9 to force them together in abutment and to close any gaps between them.

FIG. 4 provides a schematic illustration of a radiation shield 11 in a deployed configuration but without a platform flap or skirt as illustrated with regard to FIGS. 1 to 3. A platform flap or skirt is not needed if a platform 13 rests directly on a radiation source box 12 which is shielded itself. The box 12 is X-ray transparent for direct radiation only towards the platform 13. A radiation enclosure about a patient 14 is created by the shield 11 and the platform 13. The shield 11, as described above, comprises a shield carrier 16 and a shield extension 17. The carrier 16 can be part of a radiation detector or separate but in either event moves upon a displacement mechanism 15 to proximity with the patient/patient 14 with the extension 17 stowed. Once the carrier 16 is in the second position as described previously with regard to FIG. 3 then the extension 17 is deployed as previously so it extends to the platform 13 to at least close a gap 18. The extension 17 preferably engages with the platform 13 at its peripheral edge Such deployment involves the shield extension 17 rolling or otherwise being extended by lowering/falling to drape at least down to the platform 13 edges, and optionally beyond those edges, thus providing an overlap with the shielding around the at least one source 2a, 2b, 2c so as to eliminate any gap between the shield extension 17 and the source shielding, through which X-ray scatter radiation could otherwise emanate.

Figure 6:
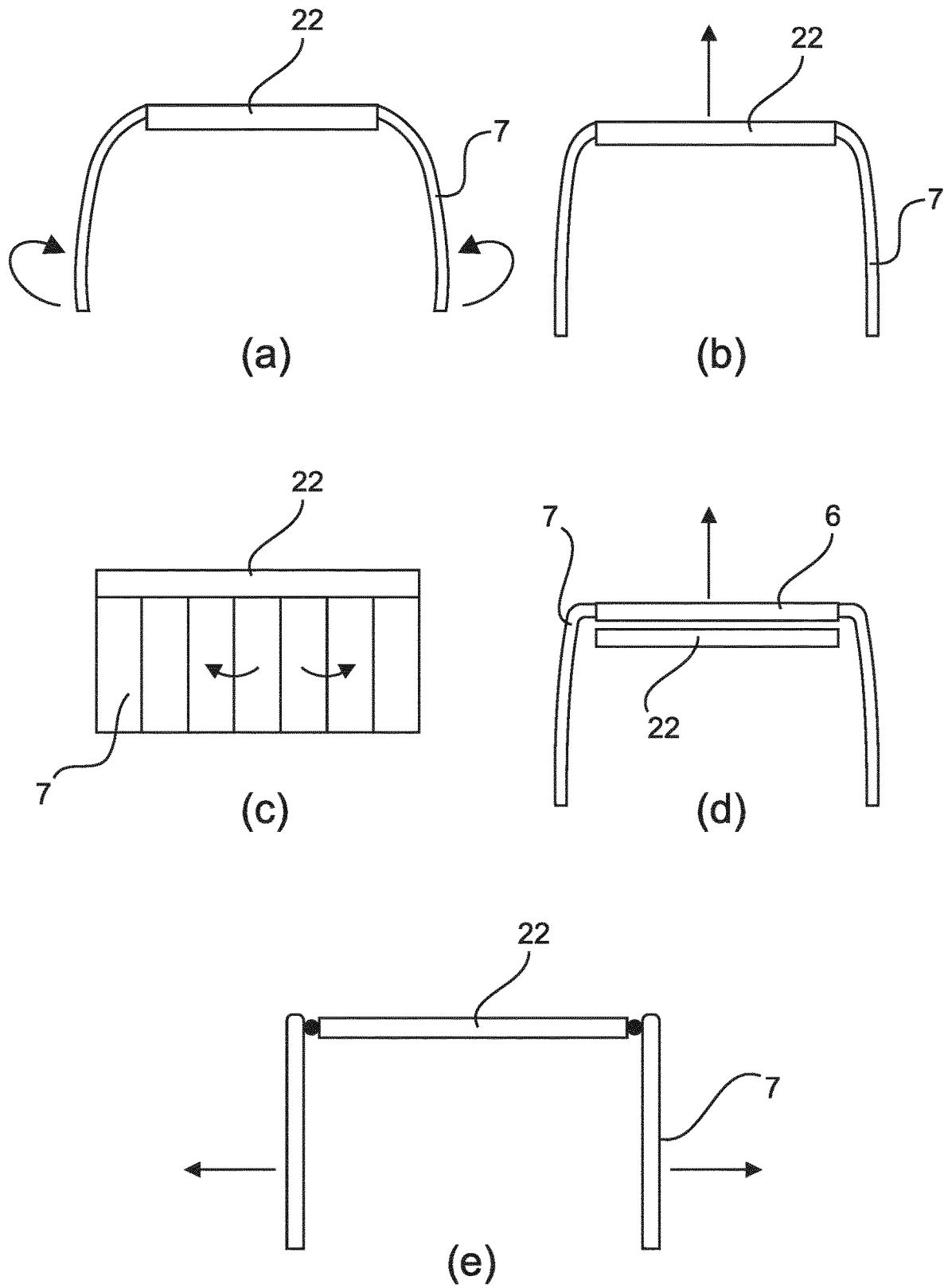
FIGS. 6(a) to 6(e) show schematic illustrations of different ways of moving the shield extensions to provide access.

FIG. 6 illustrates a number of alternative possibilities for moving the at least one shield extension 7 for access to the platform 2 and the patient 4. In FIG. 6(a), the at least shield extension 7 is able to be rolled up toward the detector 22 (and/the carrier 6). Once rolled, the at least one shield extension can be secured in its roll form by any means such as a button, Velcro, a strap, etc. In FIG. 6(b), the at least one shield extension 7 is able to be moved relative to the platform 3 and the shielding about the source 2 by raising and lowering the detector 22 to which the at least one shield extension 7 is fixed. In FIG. 7(d), the shield carrier 6 is able to be raised and lowered relative to the detector 22 to move the at least one shield extension 7. In FIG. 7(c), the shield extension 7 includes adjacent shield elements in the form of strips that hang from the carrier 6/the detector 22. The strips of the at least one shield extension 7 are able to be moved apart to provide access to the platform 3 and the patient 4. In FIG. 7(e), the at least one shield extensions 7 is removable relative to the detector 22/the shield carrier 6 to provide access to the platform 3. These alternative possibilities for moving the at least one shield extension 7 can be provided in the alternative or any two or more can be combined.

Figure 7:
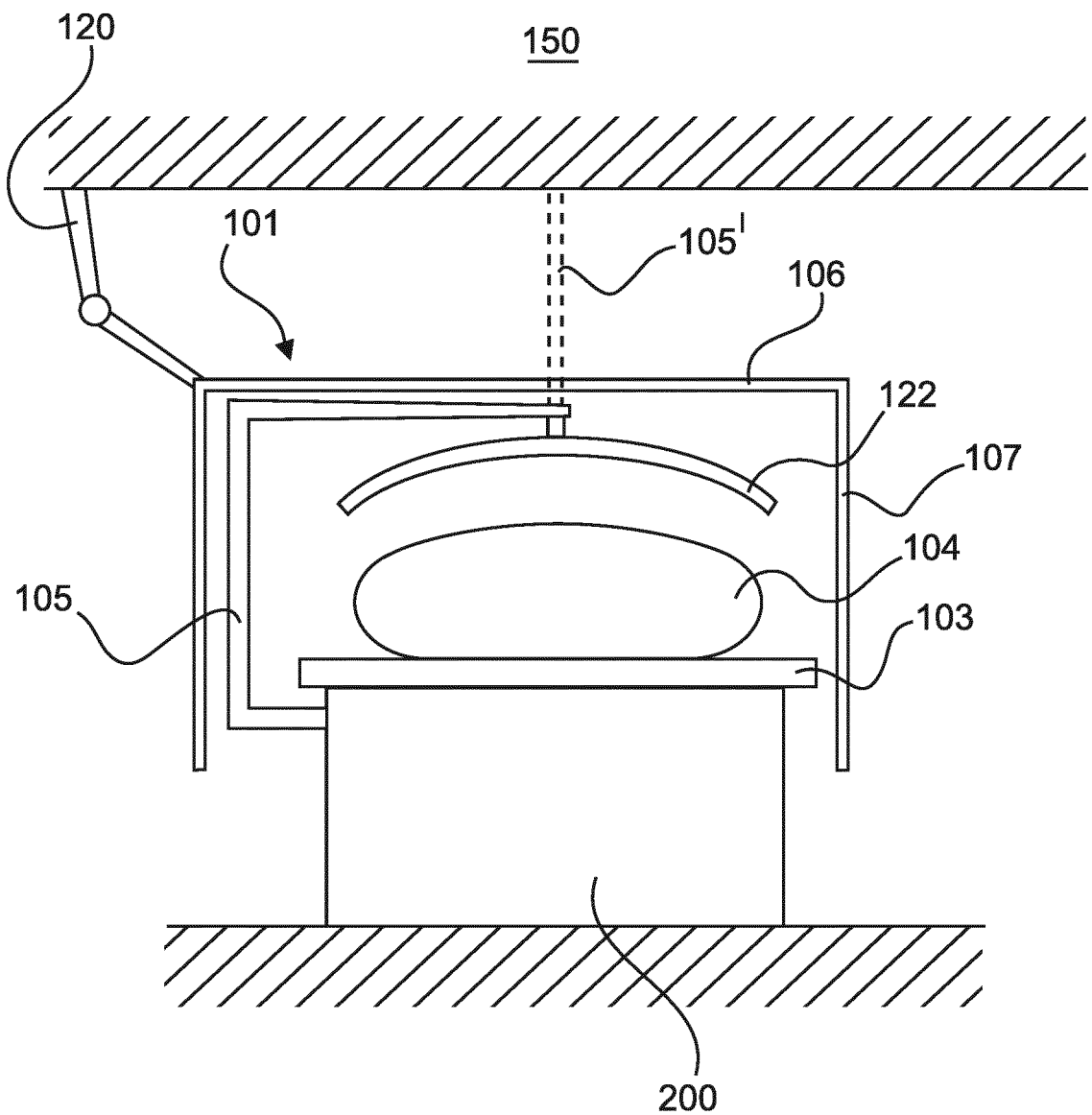
FIG. 7 shows illustration of an alternative radiation system to that of FIGS. 1 to 4.

Another alternative embodiment of a radiation system 150 is shown in FIG. 7 having a shielded enclosure 200 for at least one radiation source (not shown) onto which is disposed a patient support platform 103. From this construction, X-ray radiation is shielded below the platform 103. Further, a radiation shield includes a shield carrier 106 that is disposed above a radiation detector 122 and includes at least one shield extension 107 extending to, and slightly beyond, the platform 103 to encompass a patient 104 on the support platform 103. In this way, radiation shielding is provided between the detector 122 and the fixed shielded enclosure 200. The shield extension 107 is brought down at least to a level of the shielded enclosure 200 so that it overlaps therewith so that no gaps in the height direction exist therebetween. In the exemplary embodiment shown, the radiation shield 101 includes first and second shield extensions 107 that respectively extend on each side of the support platform 103 and shorter fringe shielding (not shown) that respectively connect the shield extensions 107 at opposed ends, thereby forming a shielded hood enclosure.

In the alternative embodiment of FIG. 7, the detector 122 is positioned relative to the shielded enclosure by a support arm 105 extending from the shielded enclosure 200 or the platform 103 to a position above the platform 103. The detector 122 is suspended from the support arm 105. In an alternative embodiment shown by dashed lines in FIG. 7, the detector 122 is suspended by a support arm 105' that is ceiling mounted. The radiation shield 101 is, in the shown exemplary embodiment, suspended from a shield support arm 120 that may be ceiling mounted as shown. The shield support arm 120 may be articulable to move the radiation shield relative to the fixed shielded enclosure 200. For example, the articulable shield support arm 120 may allow the radiation shield 101 to be moved vertically or sideways to provide access to the platform 103 and the patient 104.

The articulable shield support arm 120 may allow an operator to manually swing the shield 101 out of the way with respect to the platform 103.

As in the other embodiments, the shield extensions 7 may be retractable to a stowed configuration such as by rolling. The shield extensions 7 may be made of strip formed shield elements. Further, the shield extensions 7 may be removable from the carrier 106.

The detector 122 and/or the shield 101 may be associated with a displacement mechanism or respective displacement mechanisms to allow raising and lowering of the detector 122 and/the shield 101. Again, an automated control of an electronic (which may be motorized) displacement mechanism is possible, whereby sensed information concerning the position of the patient 104 allows automated poisoning of the detector 107 and/or the radiation shield 101.

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein the radiation shield does not act around the complete periphery of the platform and patient so scatter radiation is allowed in one direction or sector. Thus, if the suffers from claustrophobia they may have an open side to feel less confided and/or an open side may allow access by equipment not sensitive to scattered radiation. The radiation shield may be transparent so that the patient can be viewed. The shield extension may have displaceable access panels if a solid sheet of radiation absorbing or attenuating material is used and not formed of draping strips or bands of material side-by side. The shield extension may have a weighted lower edge to facilitate lowering and/or retention of the shield extension in position. The radiation shield may have fasteners or other devices to retain location of the shield extension relative to the platform and/or the platform skirt/flap if used. The shield extension may incorporate markings to show how far the shield extension has been lowered and/or act as a warning that the extension is nearly fully extended and/or to provide an indication of adequate overlap with the platform edges and/or the platform skirt/flap if used in a particular embodiment.

In another alternative, the shielded enclosure 100, 200 having the radiation sources therein may extend horizontally from below the patient support table 3, 103 (but still below table height). In addition to, or alternatively to, the shielded enclosure 100, 200 possibly being broader than the patient support table 3, 103, the patient support table 3, 103 might also be movable relative to the shielded enclosure 3, 103 for positioning a patient on the support table 3, 103 or otherwise positioning the patient and the support table 3, 103 relative to the sources 2a, 2b, 2c and the detector 22, 122. In such instances, the at least one shield extension 7, 107 is able to be arranged so as to extend to any shield skirt 9 on the broad or positionally offset patient support table 3, 103 or to a position overlapping an uppermost part of the shielded box 100, 200 and thus may need to conform to an edge of the patient support table 3, 103.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A radiation system, comprising:
   a patient support platform;
   at least one X-ray radiation source positioned on a first side of the patient support platform;
   an X-ray radiation detector positioned on a second side of the patient support platform opposite the first side;
   a fixed source X-ray radiation shield disposed about the X-ray radiation source;
   a detector X-ray radiation shield comprising a shield carrier and at least one shield extension, wherein the at least one shield extension is configured to be moved relative to the shield carrier between an extended configuration wherein the at least one shield extension extends from the shield carrier to the source radiation shield or a peripheral edge of the platform, and a stowed configuration wherein the at least one shield extension is retracted towards the shield carrier to allow access to a patient on the support platform, and
   a displacement mechanism configured to move the shield carrier towards and away from the patient support platform.

2. The radiation system of claim 1, wherein the displacement mechanism is further configured to move the radiation detector towards and away from the patient support platform.

3. The radiation system of claim 1, wherein, in the extended configuration, the at least one shield extension overlaps with the source radiation shield so as to eliminate a gap between the at least one shield extension and the source radiation shield.

4. The radiation system of claim 1, wherein the shield carrier is part of the radiation detector.

5. The radiation system of claim 1, wherein the radiation shield includes the form of a radiation shielding enclosure hood extending around the radiation detector.

6. The radiation system of claim 1, wherein the radiation shield is formed from a flexible shielding material, optionally a textile.

7. The radiation system of claim 1, wherein the at least one shield extension includes indicator elements to provide an indication of incident radiation.

8. The radiation system of claim 7, wherein the indicator elements are radiation sensitive fibers and/or electronic devices associated with the at least one shield extension.

9. The radiation system of claim 7, wherein the at least one shield extension is detachable from the shield carrier.

10. The radiation system of claim 7, wherein the at least one shield extension is formed from a plurality of shield extension elements.

11. The radiation system of claim 10, wherein the source shield comprises a platform flap or skirt extending from the patient support table that engages with the at least one shield extension.

12. The radiation system of claim 7, wherein the radiation source comprises a plurality of radiation sources providing radiation at different angles with respect to one another or a radiation source that is movable to provide radiation at different angles.

13. The radiation system of claim 7, wherein the at least one shield extension comprises first and second shield extensions respectively on opposed sides of the patient support platform that each extend to the source shield.

14. The radiation system of claim 1, including a controller and a sensor, wherein the sensor is for sensing positional information of a patient on the support platform, and the controller is responsive to the sensed positional information to control an electronic mechanism for positioning at least one of the detector, the shield and the at least one shield extension relative to the platform.

15. The radiation system of claim 1, wherein at least the shield extension of the radiation shield is wrapped or disposed within removable sterile covering material.

* * * * *